United States Patent [19]
Naylor

[11] B  3,982,277
[45] Sept. 21, 1976

[54] TIMING-ERROR COMPENSATION FOR LOW-SPEED TAPE SYSTEMS

[75] Inventor: Thomas K. Naylor, Belmont, Mass.

[73] Assignee: American Optical Corporation, Southbridge, Mass.

[22] Filed: Dec. 26, 1973

[21] Appl. No.: 427,883

[44] Published under the second Trial Voluntary Protest Program on January 20, 1976 as document No. B 427,883.

[52] U.S. Cl. .................................. 360/27; 360/36; 360/51
[51] Int. Cl.² ........................................ G11B 27/10
[58] Field of Search .................... 360/26, 27, 36, 51

[56] References Cited
UNITED STATES PATENTS

| | | | |
|---|---|---|---|
| 3,347,997 | 10/1967 | Woodruff | 360/27 |
| 3,761,646 | 9/1973 | Beauviala | 360/26 |

Primary Examiner—James W. Moffitt
Attorney, Agent, or Firm—H. R. Berkenstock, Jr.; William C. Nealon

[57] ABSTRACT

There is disclosed a technique for compensating timing errors in low-speed tape systems, such as a system in which ECG signals are recorded on a tape moving as slow as 0.08 inches per second. Clock pulses are recorded on the tape together with the signal of interest. After the signal is derived during reading of the tape, the recorded clock pulses control the sampling of the signal. The samples are used to re-constitute the signal under the control of another set of clock pulses. This latter set of clock pulses is derived from the recorded set by a phase-locked loop which establishes equal time spacings between the re-constituting clock pulses even though the sampling clock pulses, which are read from the tape and applied to the input of the phase-locked loop, may have unequal time spacings.

13 Claims, 3 Drawing Figures

TIMING-ERROR COMPENSATION FOR LOW-SPEED TAPE SYSTEMS

This invention relates to low-speed tape recorders, and more particularly to techniques for compensating for timing errors in the signals recorded on low-speed tapes.

In many applications in which tape recorders are used, there is a need for precise speed control. But there is a particular class of applications in which such control is very difficult to achieve. In general, the larger the apparatus and/or the faster the tape speed, the easier it is to achieve a constant tape speed. The problems arise in connection with small, slow-speed recorders.

Consider, for example, a portable tape recorder used to record the physiological signals of a patient, such as a portable tape recorder for recording an ECG signal. In many instances it is desirable to record the continuous ECG signals for a 24-hour period on a single standard tape cassette. To do this, the tape must be moved at well below 1 inch per second, e.g., 1/16 inch per second. It is very important that the tape speed be constant; when the tape is reviewed, the time intervals between R waves of successive beats are often measured, and these time intervals can vary greatly if the tape speed is not held constant during the recording and playback. It is necessary to keep both high-frequency (flutter) and low-frequency (wow) variations to a minimum. This is exeedingly difficult to achieve in a miniature (portable), slow-speed tape recorder.

One technique which has been used in the prior art to compensate for timing errors is to record clock signals on the same tape on which the signal of interest is recorded. These clock signals may be recorded in the same or in a different channel. Since the clock pulses occur at a fixed rate during the recording process, during playback the same clock pulses may be used to control the tape speed so that the rate of the clock pulses read from the tape remains constant. A feedback loop may be provided in the playback system for operating on the clock pulses and for deriving a control voltage which adjusts the speed of the tape drive capstan. The control voltage adjusts the capstan speed such that the clock pulses occur at a constant rate; if the tape speed is continuously adjusted so that the clock pulses occur with "perfect" periodicity, than it is assured that the signal of interest is reproduced with no timing errors. Unfortunately, the use of a feedback loop in this manner corrects only slow timing errors. While on the average the time spacings of the clock pulses may be made uniform, during short intervals of time the clock pulse spacings may not be at all uniform. In the case of an ECG signal, for example, what is important are short-range time measurements as well as long-range time measurements, and standard feedback control techniques are generally ineffective for allowing an ECG signal to be reproduced accurately from a slow-speed tape.

It is a general object of my invention to provide a technique for compensating timing errors in a signal recorded on a slow-speed tape.

A standard tape cassette speed is 1 7/8 inches per second. To record a 24-hour ECG signal on a standard cassette, however, it is necessary to move the tape at a speed of approximately 0.08 inches per second. The slower the tape speed, the lower is the highest frequency component in the signal of interest which can be recorded. Of course, the upper limit is determined by many different parameters, such as the quality of the tape heads. But to place the present invention in proper perspective, it may be said that it is applicable to the recording of signals on tapes which are moved at a speed less than 1 inch per second. At a speed of one inch per second, by utilizing the technique of the invention, signal components as high as 5 kHz can be recorded and reproduced accurately with state-of-the-art components. At even slower speeds, for example, at a speed of 0.08 inches per second, the highest frequency component which can be accurately recorded and reproduced is below 1 kHz. However, this is sufficient for the recording of most physiological signals, including ECG signals. (For the best possible performance, it is preferred to use the recorder drive and head mount mechanisms disclosed in application Ser. No. 396,025, filed on Sept. 10, 1973 and now U.S. Pat. No. 3,913,869 and application Ser. No. 396,026, filed on Sept. 10, 1973 and now U.S. Pat. No. 3,882,543, both in the name of William Richards.)

In accordance with the principles of my invention, clock pulses are recorded together with the signal of interest on the tape. (Since the recording of clock pulses simultaneously with a signal of interest on a tape is old per se, the recording technique itself is not further disclosed herein.) As is known in the prior art, during playback the clock pulses are used as the input to a feedback loop which controls the speed of the tape drive capstan. But in order to compensate for high-speed timing errors (relative to the slow-moving tape), the recorded clock pulses and the prior art feedback loop serve another function.

The analog signal itself may be recorded directly on the tape, or in the form of a modulated signal. In either case, after the original signal recorded on the tape is derived in the usual manner, it is processed further. The clock pulses are used to sample the derived signal; the clock pulses read from the tape control the operation of an input sample-and-hold circuit. A standard phase-locked loop operates on the recorded clock pulses to derive a DC voltage which, as in the prior art, is used to adjust the speed of the tape drive capstan. But the phase-locked loop also derives a clock signal which tracks the average frequency of the input clock frequency (the clock pulses read from the tape). The clock pulse waveform derived by the phase-locked loop does not exhibit the fast changes which may be exhibited in the input clock waveform; the clock pulses derived from the phase-locked loop occur with equal time spacings between them. (Although the frequency of the clock waveform at the output of the phase-locked loop might otherwise change over long periods of time, since the prior art feedback loop keeps the average tape speed constant over long periods of time, the output clock waveform varies only within tolerable limits.) The output clock pulses are used to transfer samples from the input sample-and-hold circuit to an output sample-and-hold circuit. The samples delivered to the output sample-and-hold circuit are then smoothed to provide a reproduced signal with no timing errors.

The clock pulses recorded on the tape are thus used to sample the signal of interest. Although the clock pulses do not occur at equally spaced intervals due to wow and flutter effects, since the clock pulses were recorded at equally spaced intervals they represent equally spaced samples in "real" time — even though the samples are not actually derived at equally spaced intervals in real time. It is the clock waveform at the output of the phase-locked loop which controls the reconstruction of the signal by samples which are operated upon at equally spaced intervals in real time. Synchronism between the two sample-and-hold circuits is established by the phase-locked loop since it functions to derive an accurate output clock waveform from an inaccurate input clock waveform. Of course, this technique does not assure that the frequency of the output clock waveform does not change if the frequency of the input clock waveform changes as averaged out over a relatively long time interval; such long-range changes would necessarily prevent the accurate reproduction of the signal of interest. However, because the prior art feedback loop adjusts the tape speed so that the average speed is constant over longer intervals (measured in seconds or even fractions of a second), the output clock waveform is maintained at a much more constant rate, over short time intervals as well as long ones.

In view of the foregoing description concerning the fact that the frequency of the clock waveform at the output of the phase-locked loop might change over long periods of time, but varies only within tolerable limits, and in view of the foregoing description concerning the fact that the prior art feedback loop adjusts the tapes speed so that the average speed is constant over longer intervals, it is apparent that there are established minimum and maximum tape speeds within which the system operates. Accordingly, within the system, means are provided for establishing a range of speeds within which the tape is played back, permitting a predetermined percentage variation of tape speed. It further follows from the discussion presented earlier, that the system includes other means for establishing a narrow clock rate range within which the clock rate varies; this clock rate range has a percentage variation substantially less than the percentage variation permitted by the minimum and maximum limits of the tape speed range.

Further objects, features and advantages of my invention will become apparent upon consideration of the following detailed description in conjunction with the drawing, in which.

As mentioned above, during recording and playback of ECG signals on magnetic tape, tape speed variations past the tape head result in distortion of the waveforms. Even if Hall-effect playback heads are used to eliminate gain errors, timing errors still occur. In the prior art, it has been proposed to record a reference signal of constant frequency on the tape as the ECG signal, or any other physiological signal of interest, is being recorded. Common speed variations thus affect the two signals in the same way. The resulting distortion of the reference signal can be used to correct the distortion of the ECG signal. However, in the prior art the reference signal has been used simply to control the tape speed so that "on the average" the tape speed is correct. But if it requires as much as a few seconds for the tape speed to be corrected, it is apparent that fast timing errors, especially on a very slow-moving tape, cannot be compensated.

Figure 1:
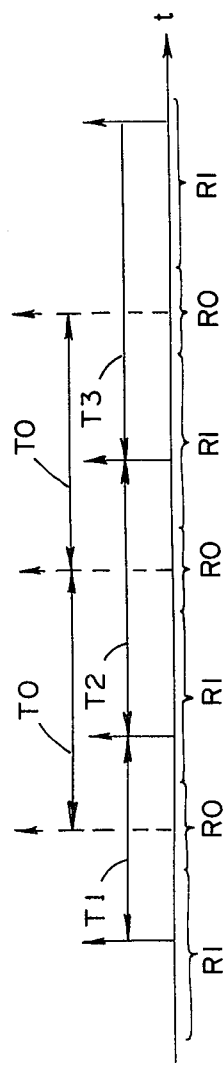
FIG. 1 is a timing waveform which depicts the operation of my invention.

FIG. 1 depicts the basic timing scheme of my invention. The solid vertical arrows represent the positions on the time axis of successive input samples. Each of these arrows corresponds to a clock pulse recorded on the tape. The four clock pulses shown in the drawing are separated by time intervals T1, T2 and T3. Although during the recording process, the clock pulses are generated at equally spaced intervals, during playback the clock pulses do not occur in perfect time step. It is assumed, however, that each clock pulse read from the tape occurs somewhere within a range of RI in real time. It is the prior art tape speed control technique that insures that each clock pulse occurs somewhere within the respective RI range. The tape speed is controlled such that slow changes are compensated. Although instantaneous errors cannot be corrected with the prior art technique, and each clock pulse may occur anywhere within its respective time range RI, the correction of the average tape speed is fast enough such that each clock pulse always occurs somewhere within its respective RI range of real time.

The ranges RO represent time ranges in real time during which input samples are transferred to the output sample-and-hold circuit. The times when the samples are transferred are represented by the longer vertical (dashed) arrows. Each of the clock pulses represented by one of these arrows occurs in the middle of its respective RO time range. Most important is the fact that these clock pulses occur at equal time intervals TO. It is the additional function of the phase-locked loop in accordance with the principles of my invention, to operate on the input clock pulses which are separated by unequal time intervals, and to derive a series of pulses which are separated by equal time intervals. The input clock pulses are used to derive samples of the analog signal of interest; although the samples are not derived at equally spaced intervals in real time during playback, it is known that the samples represent equally spaced samples of the recorded signal since the clock waveform which is recorded on the tape is generated by a standard accurate oscillator. It is the output clock pulses, which occur at equally spaced intervals in real time, that are used to reconstitute the signal from the samples which are taken under the control of the input clock waveform.

As mentioned above, this technique is effective to reproduce an accurate signal at the output of the system only if the average frequency of the output clock signal does not change; this is assured by the prior art feedback for controlling the tape speed. All that is required then to derive a reconstituted signal with no timing errors is to assure that instantaneous errors in the input clock pulse sequence do not become so great that the input clock pulses fall outside the respective RI ranges. In the illustrative embodiment of the invention, with the tape moving at a speed of .08 inches per second, and the input clock pulses occurring at a 480 Hz rate, standard state-of-the-art components and integrated circuits can be used to control the reproduction of an ECG signal with timing errors kept so low as to be of no concern.

Another way of looking at the timing waveform of FIG. 1 is to think of the ECG signal as a series of samples occurring in synchronism with the constant frequency reference signal depicted by the solid vertical arrows. Speed variations of the tape cause the positions of the played-back signal to waver back and forth about a mean or average series of positions shown by the RI ranges. If the tape drive mechanism is adequate to prevent the ranges of successive samples from overlapping, then the ECG sample occurring in any RI interval may be stored until the immediately following RO interval when it may be read out. By taking output samples (represented by the dashed arrows) in the middle of each RO range, then the samples will occur at a steady rate and the timing jitter will have been removed. In general, the frequency of the reference pulses should be at least four times as great as the highest frequency of interest in the signal to be reproduced. In the case of an ECG signal, recorded on a tape moving at 0.08 inches per second, the reference clock pulses should occur at approximately a 400 Hz or higher rate. If a square wave is recorded as the clock signal and a clock pulse is derived at the leading and trailing edge of each square wave, then the rate of the clock signal which is recorded should be 200 Hz.

Figure 2:
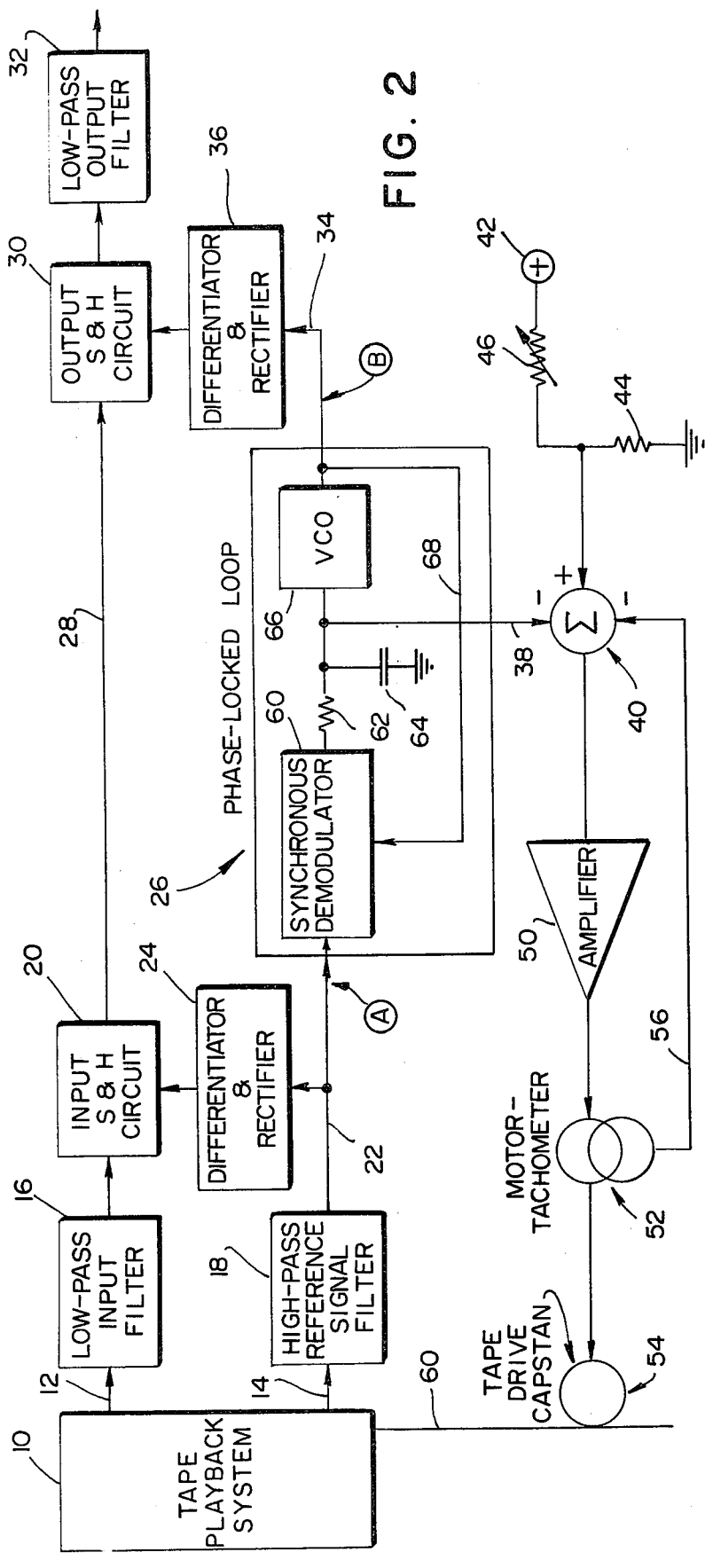
FIG. 2 is an illustrative embodiment of the invention.

FIG. 2 depicts a standard tape playback system 10 having two outputs 12 and 14. The signal of interest as well as the clock signal are recorded on tape 60, which is driven by tape drive capstan 54 (shown only symbolically on the drawing). In the illustrative embodiment of the invention, two channels on the tape are used for recording the two different signals, and the analog signal is recorded directly on the tape. Thus, during playback the analog signal appears on conductor 12 and the reference signal appears on conductor 14. However, the invention is equally applicable to a system in which the two signals are recorded on the same channel, or one in which the analog signal of interest is not recorded directly. For example, FM modulation could be used. In any case, the tape playback system must include the necessary demodulation and separation circuitry for producing two outputs — the reference clock signal on conductor 14 and the analog signal of interest (but with timing errors) on conductor 12.

The analog signal on conductor 12 is transmitted through low-pass filter 16, and the higher frequency signal on conductor 14 is transmitted through high-pass reference signal filter 18. The two filters are compensated for equal delay as is known in the art. In the case of an ECG signal, the highest frequency of interest is approximately 100 Hz; clock pulses should therefore occur at a rate at least as high as 400 Hz. The reference signal which appears on conductor 14 is a square wave having a frequency of 240 Hz. By generating a clock pulse for each zero crossing of the signal, the input clock pulses occur at a 480 Hz rate. The gain characteristic of filter 16 should thus be flat up to approximately 100 Hz, and it should then fall quickly so that the 240 Hz reference signal does not appear in the filter output. The high-pass filter 18 for the reference signal has a corner frequency at 240 Hz, and passes no part of the ECG signal.

The clock signal on conductor 22 at the output of filter 18 is differentiated, thereby producing positive and negative spikes at each zero crossing. These spikes are than rectified. Differentiator and rectifier 24 thus provides clock pulses at a 480-Hz rate, although due to timing errors the time spacings between these pulses are not uniform. These are the pulses shown by the solid arrows in FIG. 1. The ECG signal at the output of filter 16 is applied to the input of sample-and-hold circuit 20 and this standard-type circuit enters a cycle of operation each time a clock pulse is applied to its clock input by differentiator and rectifier 24. Consequently, samples of the signal of interest are taken and held in the circuit at a 480-Hz rate. Although the samples are not taken at a constant rate, they do represent equally-spaced samples of the true signal. Successive samples appear on conductor 28, extended to the signal input of output sample-and-hold circuit 30.

Figure 3:
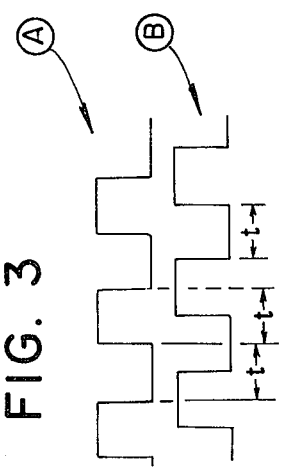
FIG. 3 is a timing waveform which will be helpful in understanding the operation of the system of FIG. 2.

The clock waveform on conductor 22 is applied to the input of phase-locked loop 26. The clock signal is shown by waveform A in FIG. 3. The phase-locked loop has two outputs 34 and 38. The output on conductor 34, shown as waveform B in FIG. 3, is similar to the input clock signal on conductor 22 with two major differences. First, the output signal is in quadrature with the input signal. Second, the phase-locked loop operates as a very narrow band-pass filter so that the frequency of the output clock signal does not follow instantaneous changes in the input clock signal. The frequency of the output clock signals remains constant provided that the average frequency of the input clock signal does not vary outside the tracking range of the loop.

The phase-locked loop, which in the illustrative embodiment of the invention is RCA type CD4046A, includes a synchronous demodulator 60, a low-pass filter consisting of resistor 62 and capacitor 64, a voltage controlled oscillator 66 and a feedback path represented by the numeral 68. The voltage at the output of the low-pass filter is slow-changing and represents the average rate of the input clock signal on input conductor 22. This DC signal is used internally to control the rate of the voltage-controlled oscillator as is known in the art, the output of the oscillator being fed back to the synchronous demodulator. The overall effect within the phase-locked loop is that the instantaneous frequency of the voltage controlled oscillator is equal to the average input frequency, with the DC voltage at the output of the low-pass filter on conductor 38 representing the average frequency of the input clock signal.

This DC signal is used to control the tape speed — to make sure that tape speed variations are constantly corrected so that each input sample (solid arrow in FIG. 1) falls within its respective sampling range RI. The feedback loop itself is known in the art. A potential source 42, potentiometer 46 and resistor 44 are used to apply a predetermined positive potential to the plus input of summer 40. From this potential there is subtracted the "error" signal on conductor 38, as well as the error signal on conductor 56. The output of the summer is extended through amplifier 50, whose output drives motor-tachometer 52. This unit not only turns the capstan but also provides a potential on conductor 56 which represents the speed of the capstan. (In the illustrative embodiment of the invention, I utilize Siemens motor No. 1AD3101-OM for unit 52.) The effect of the overall feedback loop (from the clock signal on conductor 14 to the tape drive capstan), as well as the internal feedback loop including feedback conductor 56, is to control the tape speed in accordance with the setting of potentiometer 46. The clock signal on conductor 14 is used to adjust the motor speed such that the clock pulses occur at an average rate determined by the setting of potentiometer 46, which in turn is initially set so that the average clock rate is the same as that used in the recording. This standard tape speed control loop corrects slow changes in the tape speed. As is known in the art, amplifier 50 should include a stabilizing network to prevent oscillation.

For even better speed correction, instead of using the output of the low-pass filter in the phase-locked loop as an input to summer 40, the clock signal on conductor 34 may be compared to the output of a stabilized oscillator. In such a case, an up-down counter may be used, with each pulse from the oscillator increasing the count and each step in the waveform on conductor 34 decreasing the count or vice versa. The output of the counter, a DC voltage which is proportional to the total count, may be applied to the minus input of summer 40 instead of utilizing conductor 38 for this purpose. Any of many standard feedback loops may be used for controlling the tape speed in accordance with the output pulses on conductor 14. In general, the function of the entire lower loop in the system of FIG. 2 is to ensure that the clock pulses on conductor 14 remain in their respective RI ranges in real time, even though fast changes cannot be compensated and each clock pulse may occur anywhere within its respective range.

The clock signal on conductor 34 is differentiated and rectified by differentiator and rectifier 36. Consequently, clock pulses are applied to the control input of sample-and-hold circuit 30 at a 480-Hz rate. The significant thing about these clock pulses is that they occur with equal time spacings as shown by the dashed arrows in FIG. 1. Each clock pulse causes the previously taken sample of the analog signal of interest, which is stored in sample-and-hold circuit 20 and is represented on conductor 28, to be transferred to the output sample-and-hold circuit. Thus, the samples transferred to this circuit are not only equally spaced samples of the true signal, but they are actually transferred at equally spaced intervals. The samples may then be operated upon by a standard low-pass output filter 32 to reconstitute the analog signal. The output filter filters out the 480-Hz step components at the output of the sample-and-hold circuit 30 which are introduced by the sampling process. (If the output is desired in digital form for transfer, for example, to a computer, the two sample and hold circuits can be replaced by an analog-to-digital converter followed by a first-in, first-out buffer memory. In such a case, as will be apparent to those skilled in the art, the input clock pulses would control successive conversions from analog to digital form, and the output clock pulses would control the storage of samples in the buffer memory and the reading out of the samples from the memory. With such an arrangement, output filter 32 would not be required.)

It is important to note that the clock signal on conductor 34 at the output of the phase-locked loop is in quadrature with the clock signal on conductor 22 at the input of the loop, as depicted in FIG. 3. (Although successive steps in the two waveforms are shown as occurring at intervals of $t$ seconds, it is to be understood that the timing of waveform A, at the input of the phase-locked loop, varies as described above, and that it is only the steps in the clock signal on conductor 34 that occur at equally spaced intervals.) The respective sample-and-hold circuits are triggered by both positive and negative steps in the respective waveforms. But because the two clock signals are in quadrature, a sample is transferred to the output sample-and-hold circuit between successive samples which are taken by the input sample-and-hold circuit. It is the variable delay between the taking of each sample and its transfer to the output circuit that allows the signal to be reconstituted from successive samples which occur at equally spaced intervals in real time.

The invention has been described thus far with reference to the transfer of a previously taken sample to the output circuit before another sample is taken by the input circuit. For this to be accomplished, as described above it is necessary that the tape speed be controlled such that each input clock pulse occur within its respective RI range. But if the tape speed control is not "fast" enough, it is still possible to sample the reproduced signal (on conductor 12) and then reconstruct it in accordance with the principles of the invention. In such a case, the single input sample-and-hold circuit might be replaced by two or more of such circuits so that samples of the analog signal can be stored until they are transferred serially to the output sample-and-hold circuit. The RI and RO intervals in FIG. 1 would overlap and additional storage cells would be required to store a second and perhaps even a third sample before the first is actually transferred to the output sample-and-hold circuit. The poorer the response of the tape speed feedback loop, the greater the number of samples which may have to be stored prior to their transfer to the output circuit. But in any case, the tape speed must be controlled as described. If it is not, the output clock pulses will slow down or speed up along with the input clock pulses over relatively long periods of time. The technique of my invention assures that the analog signal is reconstituted by samples which occur at equally spaced intervals in real time only if some control is exercised over the rate of the input clock pulses.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What I claim is:

1. A system for deriving a time-error compensated analog signal from a tape on which an original analog signal was recorded together with a clock signal, said clock signal having a frequency greater than the highest frequency component of interest in said original analog signal and the nominal speed of said tape being below one inch per second, comprising means for moving said tape and deriving therefrom the separate analog and clock signals recorded thereon, control means responsive to the clock signal derived from said tape for controlling the speed of said tape such that slow changes therein are compensated so that the average speed of said tape remains constant and for generating a corrected clock signal whose frequency is constant and equal to the average frequency of the clock signal derived from said tape, sampling means for taking samples of the analog signal derived from said tape in synchronism with the clock signal derived from said tape, and means controlled by the corrected generated clock signal for operating on successive samples taken by said sampling means at equally spaced intervals to reconstitute the original analog signal therefrom.

2. A system for deriving a time-error compensated analog signal in accordance with claim 1 wherein said control means includes a phase-locked loop having a low-pass filter and an oscillator therein, said low-pass filter being operative to smooth out variations in the clock signal derived from said tape so that said oscillator operates at a constant frequency to generate said corrected clock signal.

3. A system for deriving a time-error compensated analog signal in accordance with claim 2 wherein said control means includes feedback means responsive to the operation of said phase-locked loop for controlling the speed of said tape such that slow changes therein are compensated.

4. A system for deriving a time-error compensated analog signal in accordance with claim 3 wherein said control means generates said corrected clock signal with a phase which is in quadrature with the clock signal derived from said tape so that said sampling means and said reconstituting means operate alternately.

5. A system for deriving a time-error compensated analog signal in accordance with claim 4 wherein the clock signal derived from said tape and the generated corrected clock signal each represents a series of respective operating times for said sampling means and said reconstituting means, and said control means controls the speed of said tape and the generation of said corrected clock signal such that the operating times represented by the two clock signals alternate with each other and occur in mutually exclusive alternating time ranges in real time.

6. A system for deriving a time-error compensated analog signal in accordance with claim 4 wherein the clock signal derived from said tape represents a series of operating times for said sampling means, and said control means controls the speed of said tape such that each operating time represented in the clock signal derived from said tape is maintained within a respective predetermined time range during the continuous operation of said system.

7. A system for deriving a time-error compensated analog signal in accordance with claim 1 wherein said control means includes feedback means responsive to the operation of said phase-locked loop for controlling the speed of said tape such that slow changes therein are compensated.

8. A system for deriving a time-error compensated analog signal in accordance with claim 7 wherein said control means generates said corrected clock signal with a phase which is in quadrature with the clock signal derived from said tape so that said sampling means and said reconstituting means operate alternately.

9. A system for deriving a time-error compensated analog signal in accordance with claim 1 wherein said control means generates said corrected clock signal with a phase which is in quadrature with the clock signal derived from said tape so that said sampling means and said reconstituting means operate alternately.

10. A system for deriving a time-error compensated analog signal in accordance with claim 1 wherein the clock signal derived from said tape and the generated corrected clock signal each represents a series of respective operating times for said sampling means and said reconstituting means, and said control means controls the speed of said tape and the generation of said corrected clock signal such that the operating times represented by the two clock signals alternate with each other and occur in mutually exclusive alternating time ranges in real time.

11. A system for deriving a time-error compensated analog signal in accordance with claim 10 wherein the clock signal derived from said tape represents a series of operating times for said sampling means, and said control means controls the speed of said tape such that each operating time represented in the clock signal derived from said tape is maintained within a respective predetermined time range during the continuous operation of said system.

12. A system for deriving a time-error compensated analog signal in accordance with claim 1 wherein the clock signal derived from said tape represents a series of operating times for said sampling means, and said control means controls the speed of said tape such that each operating time represented in the clock signal derived from said tape is maintained within a respective predetermined time range during the continuous operation of said system.

13. A system for deriving a time-error compensated analog signal from a tape on which an original analog signal was recorded together with a first clock signal, said first clock signal having a repetition rate greater than the highest frequency component of interest in said original analog signal, said system comprising:
   first means for moving said tape and deriving separately therefrom a derived analog signal related to said original analog signal and a derived first clock signal related to said first clock signal,
   second means for establishing a tape playback speed range thereby permitting a percentage tape speed variation,
   third means for averaging the rate of said derived first clock signal,
   fourth means responsive to operation of said third means for controlling the speed of said tape to be within said playback speed range,
   fifth means for establishing a narrow clock rate range having a percentage clock rate variation substantially less than said percentage tape speed variation,
   sixth means controlled by said third means for generating a second clock signal at a rate within said narrow clock rate range,
   seventh means for taking samples of said derived analog signal in synchronism with said derived first clock signal,
   eighth means for filtering said samples to re-construct a second analog signal, and
   ninth means for transferring said samples from said seventh means to said eighth means in synchronism with said second clock signal thereby re-constructing said second analog signal with essentially no time-error distortion.

* * * * *